United States Patent
Henion et al.

[11] Patent Number: 5,856,671
[45] Date of Patent: Jan. 5, 1999

[54] CAPILLARY ELECTROPHORESIS-MASS SPECTROMETRY INTERFACE

[75] Inventors: Jack D. Henion, Trumansburg; Robin L. Sheppard, Canandaigua; Timothy Wachs, Ithaca, all of N.Y.

[73] Assignee: Cornell Research Foundation, Inc., Ithaca, N.Y.

[21] Appl. No.: 723,314

[22] Filed: Sep. 30, 1996

Related U.S. Application Data

[62] Division of Ser. No. 444,542, May 19, 1995, Pat. No. 5,587,582.

[51] Int. Cl.⁶ .............................. B01D 59/44; H01I 49/00
[52] U.S. Cl. ............................................. 250/288; 239/318
[58] Field of Search ..................................... 250/281, 282, 250/288; 239/316, 318; 222/145.5, 630, 637

[56] References Cited

U.S. PATENT DOCUMENTS

| | | | |
|---|---|---|---|
| Re. 34,757 | 10/1994 | Smith et al. ............................. | 250/288 |
| 3,608,829 | 9/1971 | Forman .................................. | 239/318 |
| 4,705,616 | 11/1987 | Andersen et al. ...................... | 250/288 |
| 4,767,058 | 8/1988 | Larosa et al. .......................... | 239/318 |
| 4,878,619 | 11/1989 | Norman ................................. | 239/318 |
| 4,901,923 | 2/1990 | Mcroskey et al. ...................... | 239/123 |
| 4,933,624 | 6/1990 | Henion et al. .......................... | 250/288 |
| 4,971,251 | 11/1990 | Dobrick et al. ......................... | 222/630 |
| 4,988,870 | 1/1991 | Diehl ...................................... | 250/288 |
| 4,994,165 | 2/1991 | Lee et al. ............................. | 204/299 R |
| 5,188,455 | 2/1993 | Hammerstedt ....................... | 222/145.5 |
| 5,344,074 | 9/1994 | Spriggs et al. ......................... | 239/318 |
| 5,352,892 | 10/1994 | Mordehai et al. ...................... | 250/288 |
| 5,505,382 | 4/1996 | Sealy et al. ............................. | 239/318 |
| 5,529,244 | 6/1996 | Horvath et al. ........................ | 239/318 |

OTHER PUBLICATIONS

Liquid Junction coupling for Capillary Zone Electrophoresis/Ion Spray Mass Spectrometry, Biomedical and Environmental Mass Spectrometry, vol. 18, 844–850 (1890).

*Primary Examiner*—Bruce Anderson
*Attorney, Agent, or Firm*—Jones, Tullar & Cooper, P.C.

[57] ABSTRACT

An interface for connecting an electrophoresis capillary to a mass spectrometer sprayer tube includes a first length of support tubing having an axial bore receiving and aligning the capillary and tube in end-abutting relationship at a junction. A solvent tube in a second length of support tubing intersects the first length of tubing in a T at the junction to supply makeup solvent to analyte flowing from the capillary to the sprayer tube. The tubing is secured in a T fitting which seals the tubing around the capillary, the sprayer tube, and the solvent tube.

16 Claims, 1 Drawing Sheet

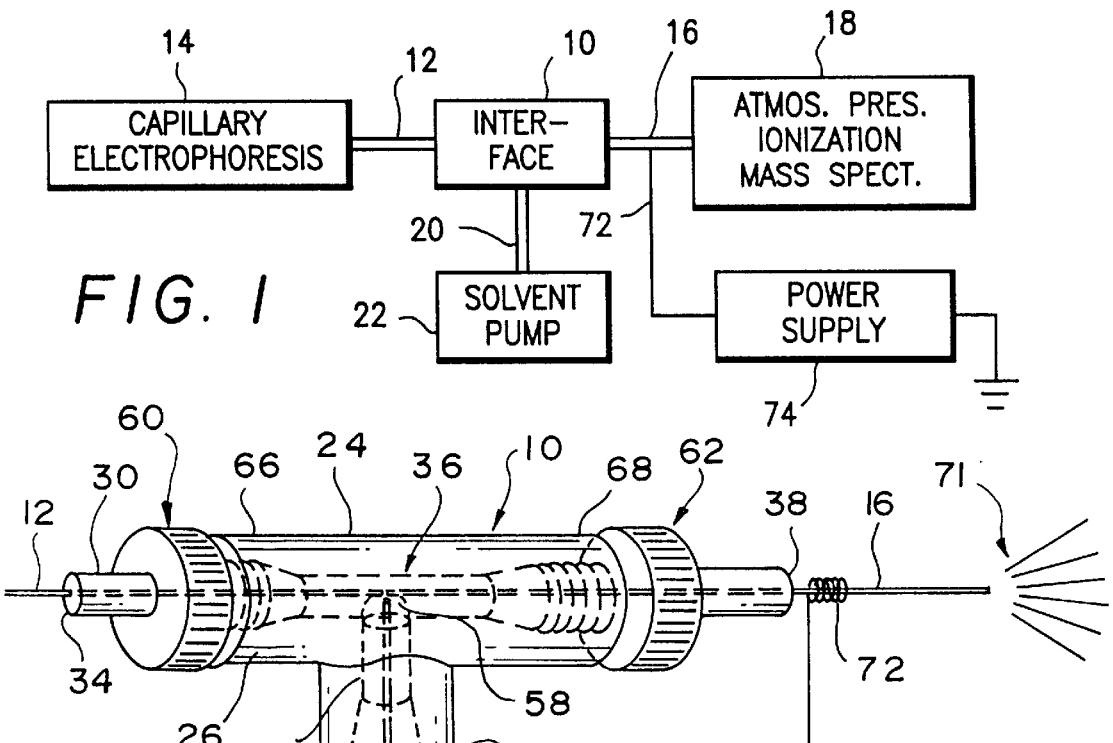
FIG. 1
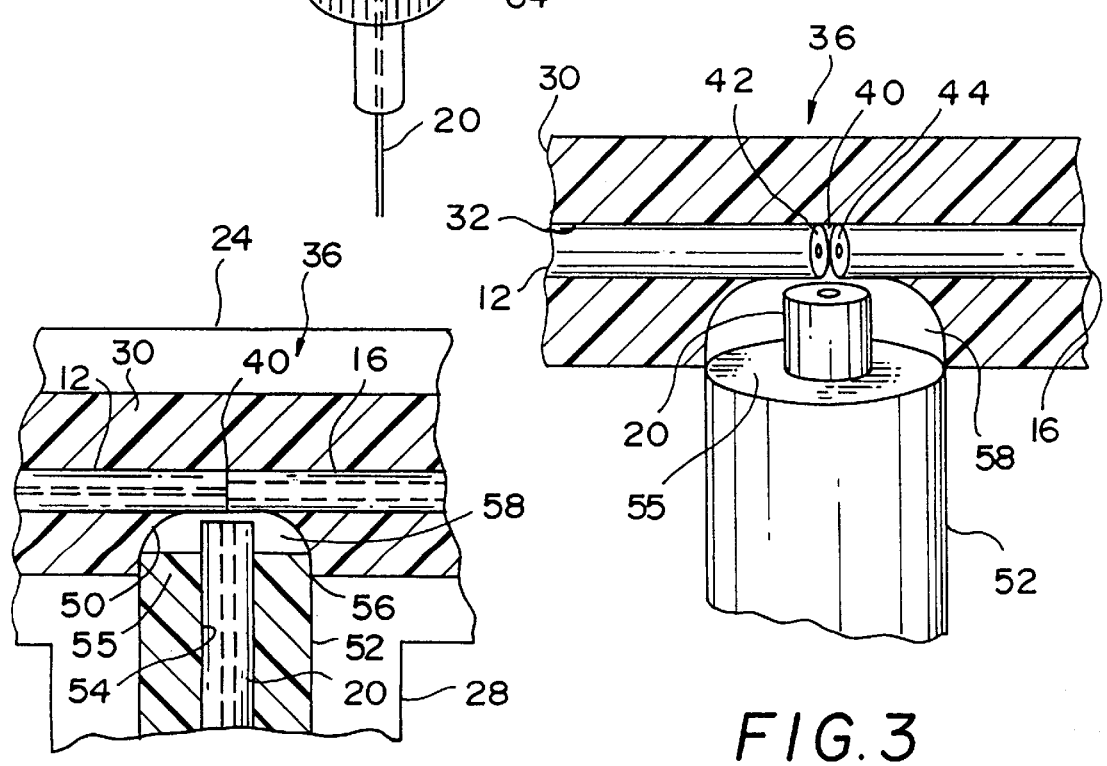
FIG. 2
FIG. 3
FIG. 4

CAPILLARY ELECTROPHORESIS-MASS SPECTROMETRY INTERFACE

This is a divisional of application Ser. No. 08/444,542 filed on May 19, 1995, now U.S. Pat. No. 5,587,582.

BACKGROUND OF THE INVENTION

The present invention relates, in general, to apparatus for coupling a capillary electrophoresis system to a mass spectrometer, and more particularly to an improved interface therefor.

Capillary electrophoresis devices are commonly used to separate electrically charged particles or molecules in solution or suspension in the presence of an applied electric field, with the particles moving toward the electrodes of opposite electrical polarity. Detection of the particles has been by the use of optical detectors based on ultraviolet absorbance and fluorescence emission, but mass spectrometry now fulfills the need for universal detection and high sensitivity. Accordingly, the solution with the entrained particles; i.e., the analytes, is directed to an atmospheric pressure ionization mass spectrometer for analysis to identify the compound or compounds in the solution. Since the mass spectrometer requires an input in the form of gas-phase ions, the analyte from the electrophoresis system has been transferred in this condensed phase from an electrophoresis capillary through a mechanism for producing ion evaporation by thermospray, fast atom bombardment, matrix-assisted laser desorption or electrospray, to the mass spectrometer. Thermospray has not been feasible because of the high liquid flow rates required for thermospray ionization and because of sensitivity limitations in comparison to other mass spectrometry ionization techniques. Fast atom bombardment techniques produce excessive band-broadening and loss of separation efficiency. Also, matrix-assisted laser desorption has so far enjoyed limited success for on-line capillary electrophoresis-mass spectrometry coupling. Finally, electrospray ionization benefits from high electrophoresis electroosmotic flows and low buffer concentrations to maintain stable electrospray conditions. Thus, the coupling of a capillary electrophoresis system to a mass spectrometer presents demanding challenges involving maintenance of flow rates while transferring an analyte from a small-diameter outlet capillary tube to an inlet, or sprayer capillary leading to the mass spectrometer.

One coupling system which attempted to meet the problems is described by J. A. Oliveres, et al in Analytical Chemistry, 59 (1987) pages 1230–1232, which describes a "sheath flow" system. However, it has been found that the sheath flow approach can suffer from incomplete mixing of the sheath and analyte, leading to ion current instability. Another approach, described by E. D. Lee et al, Biomed Environ. Mass Spectrom, 18 (1989) pages 844–850, provided a liquid junction wherein the capillary outlet from a capillary electrophoresis (CE) device is placed opposite the end of the capillary electrode of an ion spray liquid chromatograph/mass spectrometer interface device, with a 10–25 $\mu$m gap between the two pieces. The gap allowed "make-up" buffer to flow unrestricted into the ion spray interface electrode from a surrounding reservoir, preventing suction from occurring at the end of the CE device capillary. Since the flow rate into the ion spray interface was 10–20 times greater than the flow from the CE capillary, analytes from the capillary were rapidly swept into the mass spectrometer by the buffer. However, this approach required a high degree of precision in aligning and spacing the electrophoresis capillary and the sprayer.

SUMMARY OF THE INVENTION

The present invention is directed to a simplified and improved interface system for connecting an outlet capillary from an electrophoresis system to an inlet, or sprayer tube, leading to a mass spectrometer. The invention provides not only a positive and precise alignment of the capillary, with the sprayer, but also provides for a positive flow of a "makeup" or buffer solvent to ensure accuracy and stability.

In accordance with the present invention, both an outlet capillary from an electrophoresis system and a spray inlet tube leading to a mass spectrometer are secured in a single piece of support tubing having a central bore which receives both the capillary and the sprayer tube and aligns them in an abutting relationship. The facing ends of the inlet capillary and the sprayer tube both incorporate smooth, flat faces perpendicular to their axes to provide a close fit when the two are in physical abutting contact at a junction within the central bore of the tubing. A window or notch is cut into the tubing at the location of the junction to form a cavity which at least partially surrounds the junction and which receives the end of a third tube contained in a length of support tubing for supplying a solvent to the junction. This solvent is under pressure to prevent leakage of the analyte from the junction and to provide a positive flow of the analyte from the capillary to the mass spectrometer.

The support tubing which holds the capillary, the sprayer tube and the solvent supply tube is secured in a T fitting which has a top arm and a perpendicular intersecting leg. The top arm has a continuous axial bore through its length which receives and secures the inlet capillary and the sprayer tube while the perpendicular leg has a continuous axial bore which receives the solvent tube. The capillary and the tubes are secured in the T fitting with conventional compression fittings so that the tubing is swaged down around the capillary and the tubes to seal them and to secure the solvent tube with respect to the capillary and the sprayer tube. The fitting secures the solvent tube with its outlet end in the window formed at the junction of the capillary and the sprayer tube, in close proximity to the junction. Optionally, the solvent tube support tubing may fit within the window formed in the first length of tubing with a friction fit to retain solvent in the cavity surrounding the junction.

The solvent is supplied under a slight positive pressure to the window to maintain a positive flow of the analyte through the junction from the capillary electrophoresis system to the mass spectrometer The solvent makes up the difference in flow rates through the capillary and sprayer tube to aid in forcing the analyte to flow out of the sprayer tube into the spectrometer. Some back pressure may be exerted in the electrophoresis system capillary, but because of its length this pressure may not adversely affect electrophoresis. A slight pressure (a few millibar) can be applied to the inlet end of the electrophoresis capillary to counteract any backflow.

Electrical connections to the interface may be accomplished by soldering a contact to the mass spectrometer spray tubing, in the case where this tube is of metal. If the capillary is of fused silica or other non-metallic material, the electrical connection can be provided at the leg of the T.

BRIEF DESCRIPTION OF THE DRAWINGS

The foregoing, and additional objects, features, and advantages of the present invention will become apparent to those of skill in the art from a consideration of the following detailed description of a preferred embodiment thereof, taken in conjunction with the accompanying drawings, in which:

FIG. 1 is a diagrammatic illustration of a system in accordance with the present invention;

FIG. 2 is a perspective view of the interface of the present invention;

FIG. 3 is an enlarged diagrammatic, partially cut away view of a capillary sprayer tube junction in accordance with the present invention; and FIG. 4 is an enlarged cross-sectional view of the capillary-sprayer tube junction.

DESCRIPTION OF PREFERRED EMBODIMENT

As illustrated in diagrammatic form in FIG. 1, the present invention is directed to an interface 10 which is used to join an output capillary 12 leading from a capillary electrophoresis system 14 to an input sprayer tube 16 of an electrospray interface leading to an atmospheric pressure ionization or other type, mass spectrometer, the interface and the mass spectrometer being indicated generally at 18. The interface 10 provides precise alignment of capillary 12 with sprayer tube 16, and serves to minimize band broadening and loss of sensitivity in the transfer of particles to be analyzed from the electrophoresis system 14 to the mass spectrometer 18. A positive flow of the liquid from capillary 12 to tube 16 is maintained through the interface by a solvent liquid supplied to the interface through a solvent tube 20 leading from a solvent pump 22.

As illustrated in greater detail in FIGS. 2, 3, and 4, the interface 10 incorporates a fitting 24 having an upper cross arm 26 and an intersecting leg portion 28, with the capillary 12 and sprayer tube 16 passing through a continuous bore through the cross arm 26 and the solvent tube 20 passing through a continuous bore in the leg 28 to intersect at the junction of capillary 12 with tube 16. Although the fitting 24 will be described herein as a T fitting, with leg 28 perpendicular to cross arm 26, it will be understood that the angle at which the leg intersects the cross arm is not critical.

Precise alignment of the capillary 12 with tube 16 is maintained by means of a first length of support tubing 30 which is mounted in an axial bore through the arm portion 26 of the T fitting 24. The tubing 30 has an axial bore 32 which has a diameter substantially equal to the outer diameters of both capillary 12 and tube 16. The diameter is preferably constant throughout the length of the bore, but may vary to accommodate differences in the outer diameter of capillary 12 and tube 16. In the latter event, the different diameter bores would be coaxial to maintain precise alignment of the capillary with the interior of tube 16. Tubing 30 preferably is made from polyetheretherketone (PEEK), which is a chemically resistant plastic, although other materials may be used. For convenience, the tubing will be referred to as PEEK tubing. In the illustrated embodiment, the PEEK tubing 30 has an outer diameter of 0.0625 inch, while the innerbore 32 has a diameter of 0.0075 inch. The capillary 12, which may be a fused silica electrophoresis capillary having an outer diameter of about 190 microns, extends into an entrance end 34 of the PEEK tubing 30 to a central region 36 which is generally aligned with the central axis of leg portion 28 of the T fitting. Sprayer tube 16, which preferably is stainless steel, may have an outer diameter of 0.008 inch and an inner diameter of 0.004 inch. This tube extends into bore 32 from the opposite or exit end 38 of the PEEK tubing 30, extending through the bore 32 to the region 36 where it abuts the capillary 12 to form a junction 40 which is diagrammatically illustrated in FIG. 3, and illustrated in cross section in FIG. 4. As diagrammatically illustrated in FIG. 3, the end faces 42 and 44 of the capillary 12 and tube 16, respectively, are generally planar and are perpendicular to the longitudinal axis of the capillary and the tube, so that when they are abutted, as illustrated in FIG. 4, the two ends are in contact. If desired, the capillary and the tube 16 may be adjusted lengthwise to provide a small gap therebetween.

In order to facilitate the transfer of analyte from the electrophoresis system 14 to the mass spectrometer 18, a flow of solvent is added to the junction region 40. This is accomplished by forming a hemispherical notch, or window, in tubing 30. Thus notch preferably extends approximately half way through the tubing 30 and is centered on the junction 40, and is formed before the capillary 12 and spray tube 16 are inserted in tubing 30 to allow the wall of notch 50 to extend into the bore 32, thereby exposing the junction 40 to the notch when the capillary 12 and tube 16 are positioned in the PEEK tubing 30.

The solvent tube 20, described above with respect to FIG. 1 may be of fused silica, and may have an inner diameter, for example, of 100 microns and an outer diameter of 250 microns. The tube 20 preferably is secured in a second length of PEEK tubing 52 for protection, although in some embodiments the silica tube may be omitted and the PEEK tubing used alone to supply the solvent. Tube 20 is located in an axial bore 54 within tubing 52, the bore having an inner diameter of 0.01 inch to accommodate the tube. The tubing 52 preferably has the same outer diameter as tubing 30 and fits within a corresponding elongated bore in arm 28. Preferably, the diameter of the hemispherical notch 50 is the same as, or is slightly larger than, the outer diameter of tubing 52 so that the end 55 of the tubing fits within the circumference 56 of notch 50 to form an enclosed cavity 58 in the region of junction 40.

As has been described, the PEEK tubing 30 is secured in the cross arm 26 of fitting 24, which preferably is solid plastic drilled out to receive the tubing. Similarly, tubing 52 is secured in a bore drilled in leg 28 of fitting 24. The tubing 30 is oriented so that the notch 50 in arm 26 is aligned with the leg 28 of the fitting, and thus with the tubing 52. Standard PEEK ferrule and nut assemblies 60, 62, and 64 are provided at the ends 66, 68, and 70 of the fitting, respectively, to secure the PEEK tubing in the fitting. The nuts are threaded tightly enough to cause the ferrules to swage down the PEEK tubing at the ends of the fitting to tightly secure the capillaries 12, 16, and 20 within the tubing.

A positive flow of analyte from the electrophoresis system 14 to the mass spectrometer 18 is maintained through capillary 12, through junction 40, and through sprayer tube 16 by pumping an appropriate solvent through tube 20 into the cavity 58 and to the junction 40. The electrophoresis capillary 12 and the sprayer tube 16 can be physically in contact with each other, since pumping the solvent into the T will force a flow out the sprayer tube 16. The sprayer tube may be, for example, an electrospray needle which sprays ions 71 for delivery to the mass spectrometer.

Electrical contact for the electrospray needle 16 can be by way of a wire 72 soldered to the needle, in the case where it is stainless steel or other electrically conductive material. If the sprayer 16 is of a nonmetal material such as fused silica, a short metal tube can be inserted into leg 52 of the T and electrical contact made with that tube. The connection 72, or the connection to a tube in leg 52 is connected to a suitable power supply 74, as illustrated in FIG. 1. In the case where an electrical connection is made to the system through a tube in leg 52, an insulating union is used to connect the solvent pump system 22 to the metal conductor.

Although the present invention has been described in terms of a preferred embodiment, it will be apparent that modifications and variations may be made without departing from the true spirit and scope thereof, as set forth in the following claims.

What is claimed is:

1. A liquid junction, comprising:

a fitting;

a support tube having an axial bore extending through said fitting, said support tube bore having an entrance end for receiving an entry tube and an exit end for receiving an exit tube;

a window in said support tube intersecting said axial bore within said fitting; and a make-up tube in said fitting, said make-up tube having an axis which intersects said first axial bore at said window, said support tube serving to align said entry and exit tubes in end to end relationship at a junction within said axial bore and in said window, said make-up tube terminating at said window.

2. The junction of claim 1, further including a second support tube in said fitting and receiving said make-up tube, said second support tube terminating at said window.

3. The junction of claim 1, wherein said axial bore has a constant diameter from said entrance end to said exit end.

4. The junction of claim 1, wherein said axial bore has an entrance end having a first diameter and an exit end having a second diameter, said entrance and exit ends being coaxial.

5. A liquid junction, comprising:

a T fitting having a top arm and an intersecting leg, said top arm and said intersecting leg having respective axial bores;

a support tube having a longitudinal axis, an entrance end and an exit end, said support tube extending through said top arm axial bore;

a liquid supply tube located in said entrance end of said support tube;

a liquid outlet tube located in said exit end of said support tube, said supply tube and said outlet tube meeting in end-to-end relationship at a junction within said support tube and being axially aligned by said support tube;

a window in said support tube at said junction; and a fluid supply tube having a longitudinal axis and extending into said axial bore of said intersecting leg of said T fitting, said axis of said fluid supply tube intersecting said axis of said support tube at said window whereby fluid can be supplied to said junction of said liquid supply tube and said liquid outlet tube.

6. The junction of claim 5, wherein said window comprises a cavity surrounding said junction.

7. The junction of claim 6, wherein said fluid supply tube has an end located adjacent said junction.

8. The junction of claim 7, further including connectors which swage said support tube against said supply tube and against said outlet tube.

9. The junction of claim 8, wherein said support tube includes a continuous axial bore of constant diameter.

10. The junction of claim 9, wherein said support tube is polyetheretherketone.

11. The junction of claim 10, wherein said liquid supply tube is fused silica.

12. The junction of claim 11, wherein said outlet tube is stainless steel.

13. The junction of claim 10, wherein said liquid supply tube, said liquid outlet tube, and said fluid supply tube are fused silica.

14. The junction of claim 5, further including connectors forming liquid seals between said support tube and said T fitting.

15. The junction of claim 5, wherein said support tube has an inner diameter which closely matches the outer diameter of said liquid supply and liquid outlet tubes.

16. An interface system for interconnecting tubes, comprising:

a first arm having first and second ends, a longitudinal axis, and a continuous axial bore:

a second arm having first and second ends, a longitudinal axis, and a continuous axial bore, the axial bore of said second arm intersecting said axial bore of said first arm;

a support tube in said axial bore of said first arm, said support tube including an axial bore and having an entrance end and an exit end;

a liquid supply tube located in said support tube axial bore at said entrance end;

a liquid outlet tube located in said support tube bore at said exit end, said liquid supply tube and said liquid outlet tube meeting in end-to-end relationship at a junction within said support tube and being axially aligned by said support tube, said junction being located at the intersection of said bores of said first and second arms; and a fluid supply tube located in said axial bore of said second arm.

* * * * *